(12) United States Patent
Crook

(10) Patent No.: US 8,491,598 B2
(45) Date of Patent: Jul. 23, 2013

(54) SURGICAL POSITIONING ASSEMBLY AND ASSOCIATED SPINAL IMPLANT DEVICE AND SURGICAL METHODS

(75) Inventor: David Crook, Mineola, TX (US)

(73) Assignee: US Spine, Inc., Salt Lake City, UT (US)

( * ) Notice: Subject to any disclaimer, the term of this patent is extended or adjusted under 35 U.S.C. 154(b) by 731 days.

(21) Appl. No.: 12/396,761

(22) Filed: Mar. 3, 2009

(65) Prior Publication Data

US 2009/0234364 A1 Sep. 17, 2009

Related U.S. Application Data

(60) Provisional application No. 61/033,079, filed on Mar. 3, 2008.

(51) Int. Cl.
*A61B 17/58* (2006.01)
*A61B 17/60* (2006.01)
*A61F 2/00* (2006.01)

(52) U.S. Cl.
USPC ............... 606/99; 606/86 A; 606/914

(58) Field of Classification Search
USPC ........................... 606/99, 914, 86 A
See application file for complete search history.

(56) References Cited

U.S. PATENT DOCUMENTS

| | | | |
|---|---|---|---|
| 2007/0225726 A1* | 9/2007 | Dye et al. | 606/99 |
| 2008/0077150 A1* | 3/2008 | Nguyen | 606/85 |
| 2008/0109005 A1* | 5/2008 | Trudeau et al. | 606/99 |

* cited by examiner

*Primary Examiner* — Andrew Yang
(74) *Attorney, Agent, or Firm* — Phillips Ryther & Winchester; Matthew D. Thayne

(57) ABSTRACT

The present invention provides a surgical positioning assembly that is used to place a spinal implant device or the like within an intervertebral space or the like of a patient and associated surgical methods. Advantageously, the surgical positioning assembly allows access to the implantation site to be gained along a first axis, with the implant device subsequently being placed along a second axis that is disposed at an angle or substantially perpendicular to the first axis via the actuation of the surgical positioning assembly. Thus, for example, a surgeon may use an anterior or posterior approach to place an implant device laterally, or vice versa.

9 Claims, 4 Drawing Sheets

SURGICAL POSITIONING ASSEMBLY AND ASSOCIATED SPINAL IMPLANT DEVICE AND SURGICAL METHODS

CROSS-REFERENCE TO RELATED APPLICATION(S)

The present non-provisional patent application/patent claims the benefit of priority of U.S. Provisional Patent Application No. 61/033,079, filed on Mar. 3, 2008, and entitled "POSTERIOR LATERAL POSITIONING DEVICE AND ASSOCIATED IMPLANT DEVICE POSITIONING METHODS," the contents of which are incorporated in full by reference herein.

FIELD OF THE INVENTION

The present invention relates generally to a surgical positioning assembly that is used to place a spinal implant device or the like within an intervertebral space or the like of a patient and associated surgical methods. Advantageously, the surgical positioning assembly allows access to the implantation site to be gained along a first axis, with the implant device subsequently being placed along a second axis that is disposed at an angle or substantially perpendicular to the first axis via the actuation of the surgical positioning assembly. Thus, for example, a surgeon may use an anterior or posterior approach to place an implant device laterally, or vice versa.

BACKGROUND OF THE INVENTION

Interbody fusion is a surgical spinal procedure that places a porous metallic, plastic, or composite cage device and/or bone graft between adjacent vertebrae in the area usually occupied by an intervertebral disc, maintaining spinal alignment and disc height. Anterior lumbar interbody fusion (ALIF) is a spinal fusion procedure that utilizes an anterior (i.e. front) approach through the abdomen region to fuse adjacent vertebrae of the lumbar spine. Likewise, posterior lumbar interbody fusion (PLIF) is a spinal fusion procedure that utilizes a posterior (i.e. rear) approach through the back region to fuse adjacent vertebrae of the lumbar spine. 360-degree fusion and other similar procedures are a combination/variation of ALIF and PLIF. The intervertebral disc is removed using appropriate rasping and grasping tools and replaced with a cage device and/or bone graft after appropriate distraction and spacing tools are used to restore the normal height of the intervertebral space. ALIF is preferred when either one or multiple spinal levels are being fused and one or multiple intervertebral discs must be removed, and may be performed in conjunction with a posterior decompression (i.e. a laminectomy) and/or the placement of stabilizing instrumentation (i.e. screws and rods, plates, etc.). Because during ALIF the spinal nerves and other neurologic structures do not have to be retracted, wide access to the intervertebral space(s) of interest is provided without unacceptable risk of neurologic injury. ALIF is used to treat a variety of painful spinal conditions, such as spondylolisthesis and degenerative disc disease, among others. PLIF is also preferred when either one or multiple spinal levels are being fused and one or multiple intervertebral discs must be removed, and may be performed in conjunction with the placement of stabilizing instrumentation (i.e. screws and rods, plates, etc.). PLIF is also used to treat a variety of painful spinal conditions, such as spondylolisthesis and degenerative disc disease, among others. In either and all cases, it is often desirable to place an implant device laterally, that is, at an angle or substantially perpendicular to the anterior or posterior access axes, or vice versa.

Conventional cage devices typically include some sort of retention mechanism to hold them securely in the intervertebral space. Such retention mechanisms include biting and locking structures that engage the endplate(s) of the vertebral body or bodies of interest, screw assemblies that engage the vertebral body or bodies of interest, plate structures that engage the vertebral body or bodies of interest, etc. All of these cages and retention mechanisms, however, suffer from the shortcomings that they are difficult to place, difficult to deploy, and/or tend to allow the associated cage device and/or bone graft to shift over time and thus fail to adequately maintain the normal height of the intervertebral space, for example. Again, for these and other reasons, it is often desirable to place an implant device laterally, that is, at an angle or substantially perpendicular to the anterior or posterior access axes, or vice versa.

BRIEF SUMMARY OF THE INVENTION

Again, in various exemplary embodiments, the present invention provides a surgical positioning assembly that is used to place a spinal implant device or the like within an intervertebral space or the like of a patient and associated surgical methods. Advantageously, the surgical positioning assembly allows access to the implantation site to be gained along a first axis, with the implant device subsequently being placed along a second axis that is disposed at an angle or substantially perpendicular to the first axis via the actuation of the surgical positioning assembly. Thus, for example, a surgeon may use an anterior or posterior approach to place an implant device laterally, or vice versa.

In one exemplary embodiment, the present invention provides a surgical positioning assembly operable for positioning a surgical implant device within an implantation site in the body of a patient through an incision and/or portal, including: a grip operable for holding the surgical positioning assembly along a first axis through incision and/or portal; a retention mechanism operable for selectively coupling the surgical implant device to the grip and holding the surgical implant device substantially along the first axis; and a pivot/rotation mechanism operable for one or more of selectively pivoting and selectively rotating the surgical implant device relative to the grip until it is substantially along a second axis that is one or more of disposed at an angle to and rotated relative to the first axis. Optionally, the retention mechanism includes one or more rod structures including one or more of a hook structure and a saddle structure. Optionally, the surgical implant device includes one or more bar structures that selectively engage the one or more rod structures via the one or more hook structures and saddle structures. Optionally, the pivot/rotation mechanism includes one or more rod structures including one or more of a hook structure and a saddle structure. Optionally, the surgical implant device includes one or more bar structures that selectively engage the one or more rod structures via the one or more hook structures and saddle structures. Optionally, the surgical implant device is an intervertebral cage.

In another exemplary embodiment, the present invention provides a surgical implant device for implantation within an implantation site in the body of a patient through an incision and/or portal, including: one or more retention structures operable for selectively coupling the surgical implant device to a retention mechanism of a surgical positioning assembly and holding the surgical implant device substantially along a first axis associated with the surgical positioning assembly; and one or more pivot/rotation structures operable for selectively engaging a pivot/rotation mechanism of the surgical positioning assembly and by which the surgical implant device is one or more of selectively pivoted and selectively rotated relative to the surgical positioning assembly until it is substantially along a second axis associated with the surgical positioning assembly that is one or more of disposed at an angle to and rotated relative to the first axis. Optionally, the retention mechanism of the surgical positioning assembly includes one or more rod structures including one or more of a hook structure and a saddle structure. Optionally, the one or more retention structures include one or more bar structures that selectively engage the one or more rod structures of the surgical positioning assembly via the one or more hook structures and saddle structures. Optionally, the pivot/rotation mechanism of the surgical positioning assembly includes one or more rod structures including one or more of a hook structure and a saddle structure. Optionally, the one or more pivot/rotation structures include one or more bar structures that selectively engage the one or more rod structures of the surgical positioning assembly via the one or more hook structures and saddle structures. Optionally, the surgical implant device is an intervertebral cage.

In a further exemplary embodiment, the present invention provides a surgical method for positioning a surgical implant device within an implantation site in the body of a patient through an incision and/or portal using a surgical positioning assembly, including: disposing the surgical positioning assembly and surgical implant device through the incision and/or portal and adjacent to the implantation site along a first axis; actuating the surgical positioning assembly to pivot/rotate the surgical implant device relative to the surgical positioning assembly and into the implantation site along a second axis that is disposed one or more of at an angle to, substantially perpendicular to, and rotated with respect to the first axis; and actuating the surgical positioning assembly to disengage the surgical implant device from the surgical positioning assembly.

BRIEF DESCRIPTION OF THE DRAWINGS

The present invention is illustrated and described herein with reference to the various drawings, in which like reference numbers are used to denote like assembly/device components and/or method steps, as appropriate, and in which.

DETAILED DESCRIPTION OF THE INVENTION

Again, in various exemplary embodiments, the present invention provides a surgical positioning assembly that is used to place a spinal implant device or the like within an intervertebral space or the like of a patient and associated surgical methods. Advantageously, the surgical positioning assembly allows access to the implantation site to be gained along a first axis, with the implant device subsequently being placed along a second axis that is disposed at an angle or substantially perpendicular to the first axis via the actuation of the surgical positioning assembly. Thus, for example, a surgeon may use an anterior or posterior approach to place an implant device laterally, or vice versa.

Figure 1:
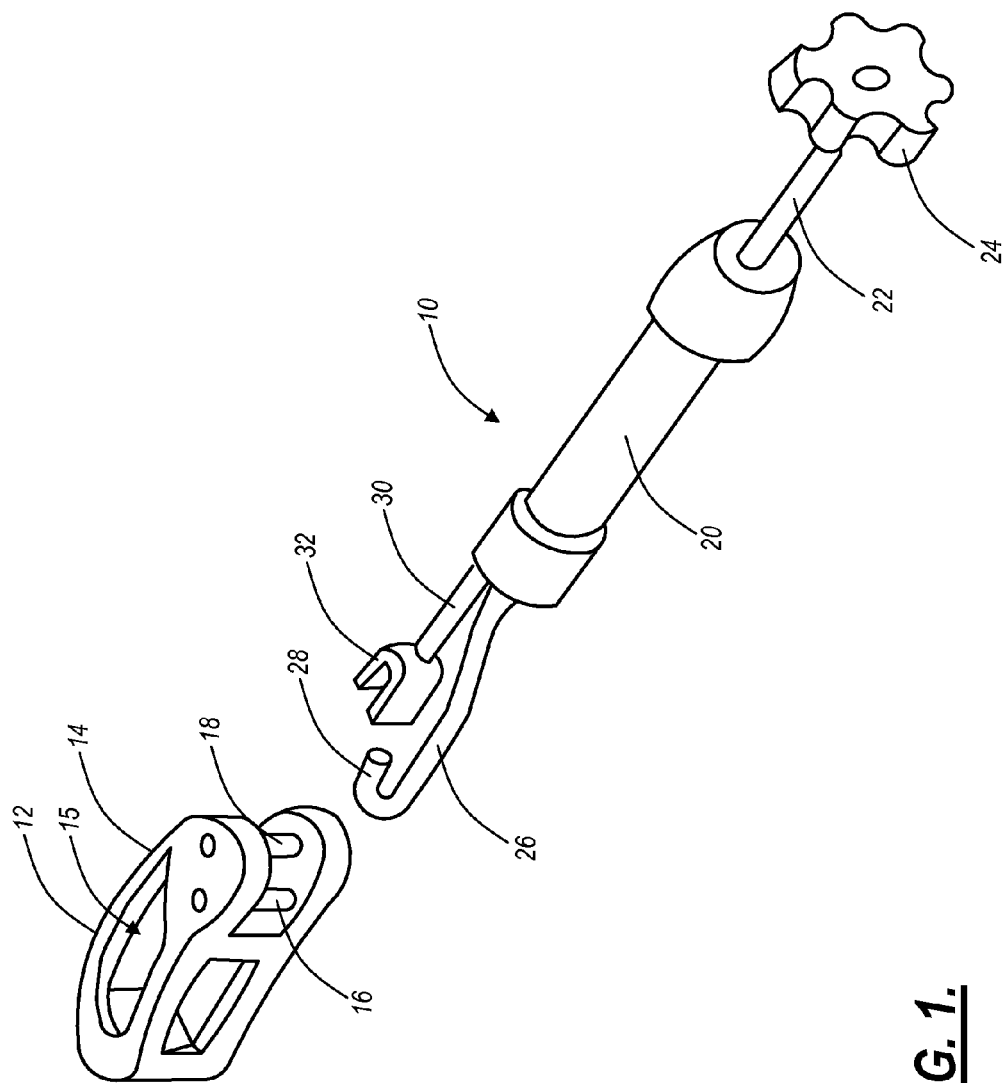
FIG. 1 is a perspective view illustrating one exemplary embodiment of the surgical positioning assembly and spinal implant device of the present invention, the surgical positioning assembly and spinal implant device illustrated in a disassembled state.

Referring to FIG. 1, in one exemplary embodiment, the present invention provides a surgical positioning assembly 10 and a spinal implant device 12. In the most broad sense, the surgical positioning assembly 10 is operable for accessing an implantation site along a first axis, with the spinal implant device 12 subsequently being placed along a second axis that is disposed at an angle or substantially perpendicular to the first axis via the actuation of the surgical positioning assembly 10. In the most narrow sense, the spinal implant device 12 is an intervertebral cage or the like and is configured and sized accordingly. However, it will be readily apparent to those of ordinary skill in the art that the surgical positioning assembly 12 may be used to place any suitable implant device within any suitable implantation site, intervertebral cage or non-intervertebral cage/spinal or non-spinal, and the first and second axes along which access and placement are carried out may be those associated with any suitable surgical approach, provided that the second axis is disposed at an angle to, substantially perpendicular to, and/or simply rotated with respect to the first axis via the actuation of the surgical positioning assembly 12.

In this exemplary embodiment, the spinal implant device 12 consists of a biocompatible structure 14 that defines a plurality of openings 15 in which a bone graft or the like may be placed, representing an intervertebral cage or the like. Thus, the spinal implant device 12 has a rounded prismatic or other suitable shape, and has a thickness on the order of millimeters to centimeters. The spinal implant device 12 includes a draw bar 16 and a pivot bar 18 by which the spinal implant device 12 is grasped and pivoted by and relative to the surgical positioning assembly 10. Again, the spinal implant device 12 may include any suitable structures by which it is grasped and pivoted and/or rotated by and relative to the surgical positioning assembly 10 upon the actuation of the surgical positioning assembly 10.

In this exemplary embodiment, the surgical positioning assembly 10 consists of an annular grip 20 by which it is positioned and held in an incision site, a partially threaded rod 22 disposed through the annular grip 20, and a draw knob 24 attached to one end of the partially threaded rod 22. The other end of the partially threaded rod 22 terminates in a draw rod 26 and hook structure 28. The hook structure is configured and sized to selectively retain the draw bar 16 of the spinal implant device 12. The surgical positioning assembly 10 also includes a pivot rod 30 attached to the annular grip 20, the pivot rod 30 terminating in a saddle structure 32 that is configured and sized to selectively retain the pivot bar 18 of the spinal implant device 12. In operation, the draw knob 24 is selectively actuated, causing the partially threaded rod 22, the draw rod 26, and the hook structure 28 to recede towards/into the annular grip 20, thereby pulling the draw bar 16. This causes the spinal implant device 12 to pivot about the pivot bar 18 disposed in the saddle structure 32, which is stationary. The draw knob 24 or another mechanism may be used to disengage the surgical positioning assembly 10 from the spinal implant device 12 once it is pivoted/rotated and placed. Again, the surgical positioning assembly 10 may include any suitable structures by which it grasps and pivots and/or rotates the spinal implant device 12 upon the actuation of the surgical positioning assembly 10.

Figure 2:
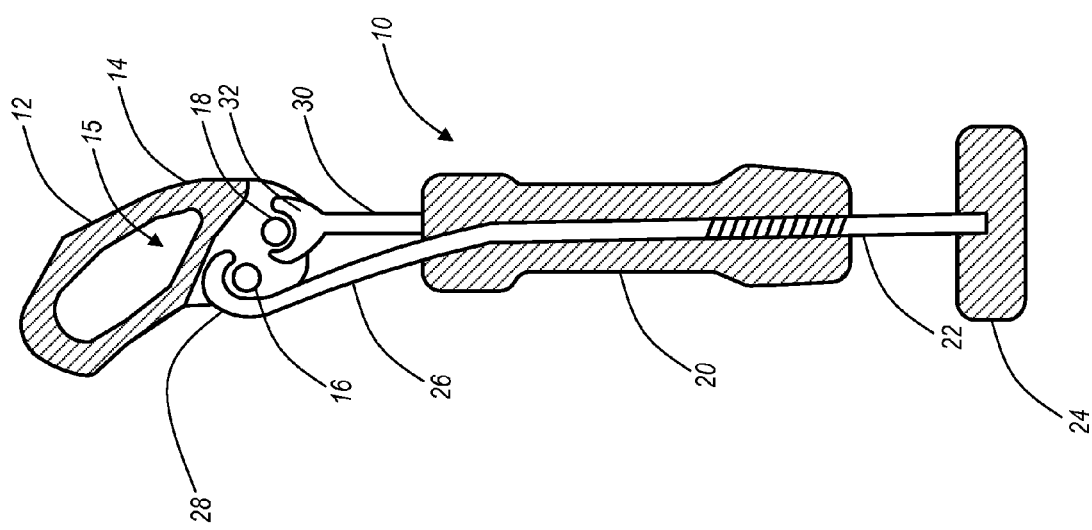
FIG. 2 is a partial cross-sectional view illustrating the surgical positioning assembly and spinal implant device of FIG. 1, the surgical positioning assembly and spinal implant device illustrated in an assembled, but undeployed, state.

Referring to FIG. 2, again, the spinal implant device 12 consists of a biocompatible structure 14 that defines a plurality of openings 15 in which a bone graft or the like may be placed, representing an intervertebral cage or the like. Thus, the spinal implant device 12 has a rounded prismatic or other suitable shape, and has a thickness on the order of millimeters to centimeters. The spinal implant device 12 includes a draw bar 16 and a pivot bar 18 by which the spinal implant device 12 is grasped and pivoted by and relative to the surgical positioning assembly 10.

The surgical positioning assembly 10 consists of an annular grip 20 by which it is positioned and held in an incision site, a partially threaded rod 22 disposed through the annular grip 20, and a draw knob 24 attached to one end of the partially threaded rod 22. The other end of the partially threaded rod 22 terminates in a draw rod 26 and hook structure 28. The hook structure is configured and sized to selectively retain the draw bar 16 of the spinal implant device 12. The surgical positioning assembly 10 also includes a pivot rod 30 attached to the annular grip 20, the pivot rod 30 terminating in a saddle structure 32 that is configured and sized to selectively retain the pivot bar 18 of the spinal implant device 12. In operation, the draw knob 24 is selectively actuated, causing the partially threaded rod 22, the draw rod 26, and the hook structure 28 to recede towards/into the annular grip 20, thereby pulling the draw bar 16. This causes the spinal implant device 12 to pivot about the pivot bar 18 disposed in the saddle structure 32, which is stationary. The draw knob 24 or another mechanism may be used to disengage the surgical positioning assembly 10 from the spinal implant device 12 once it is pivoted/rotated and placed.

Figure 3:
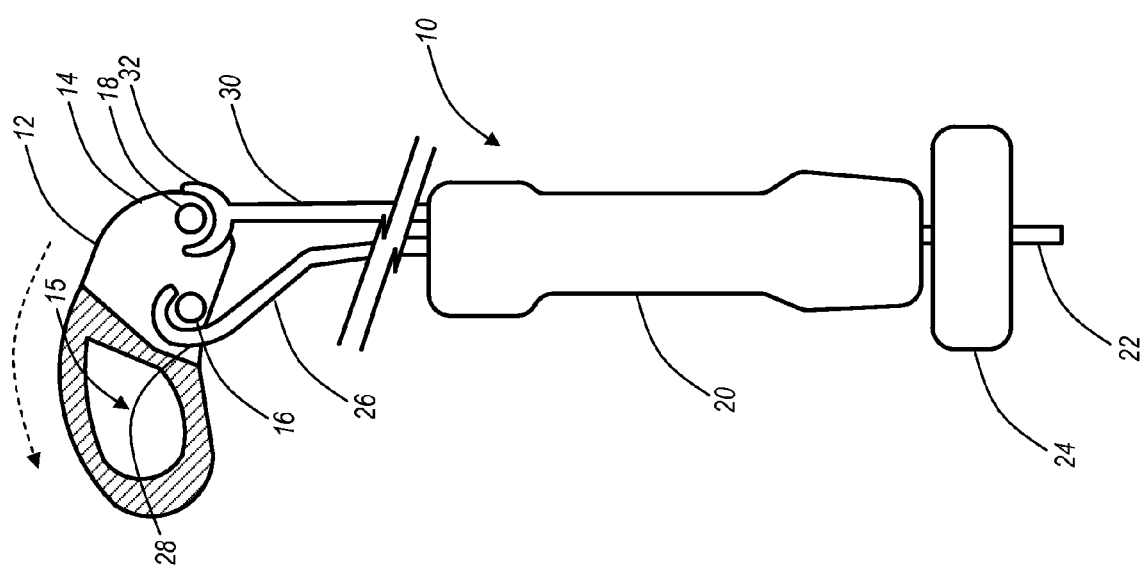
FIG. 3 is another partial cross-sectional view illustrating the surgical positioning assembly and spinal implant device of FIGS. 1 and 2, the surgical positioning assembly and spinal implant device illustrated in an assembled, and deployed, state.

Referring to FIG. 3, again, the spinal implant device 12 consists of a biocompatible structure 14 that defines a plurality of openings 15 in which a bone graft or the like may be placed, representing an intervertebral cage or the like. Thus, the spinal implant device 12 has a rounded prismatic or other suitable shape, and has a thickness on the order of millimeters to centimeters. The spinal implant device 12 includes a draw bar 16 and a pivot bar 18 by which the spinal implant device 12 is grasped and pivoted by and relative to the surgical positioning assembly 10.

The surgical positioning assembly 10 consists of an annular grip 20 by which it is positioned and held in an incision site, a partially threaded rod 22 disposed through the annular grip 20, and a draw knob 24 attached to one end of the partially threaded rod 22. The other end of the partially threaded rod 22 terminates in a draw rod 26 and hook structure 28. The hook structure is configured and sized to selectively retain the draw bar 16 of the spinal implant device 12. The surgical positioning assembly 10 also includes a pivot rod 30 attached to the annular grip 20, the pivot rod 30 terminating in a saddle structure 32 that is configured and sized to selectively retain the pivot bar 18 of the spinal implant device 12. In operation, the draw knob 24 is selectively actuated, causing the partially threaded rod 22, the draw rod 26, and the hook structure 28 to recede towards/into the annular grip 20, thereby pulling the draw bar 16. This causes the spinal implant device 12 to pivot about the pivot bar 18 disposed in the saddle structure 32, which is stationary. The draw knob 24 or another mechanism may be used to disengage the surgical positioning assembly 10 from the spinal implant device 12 once it is pivoted/rotated and placed.

Figure 4:
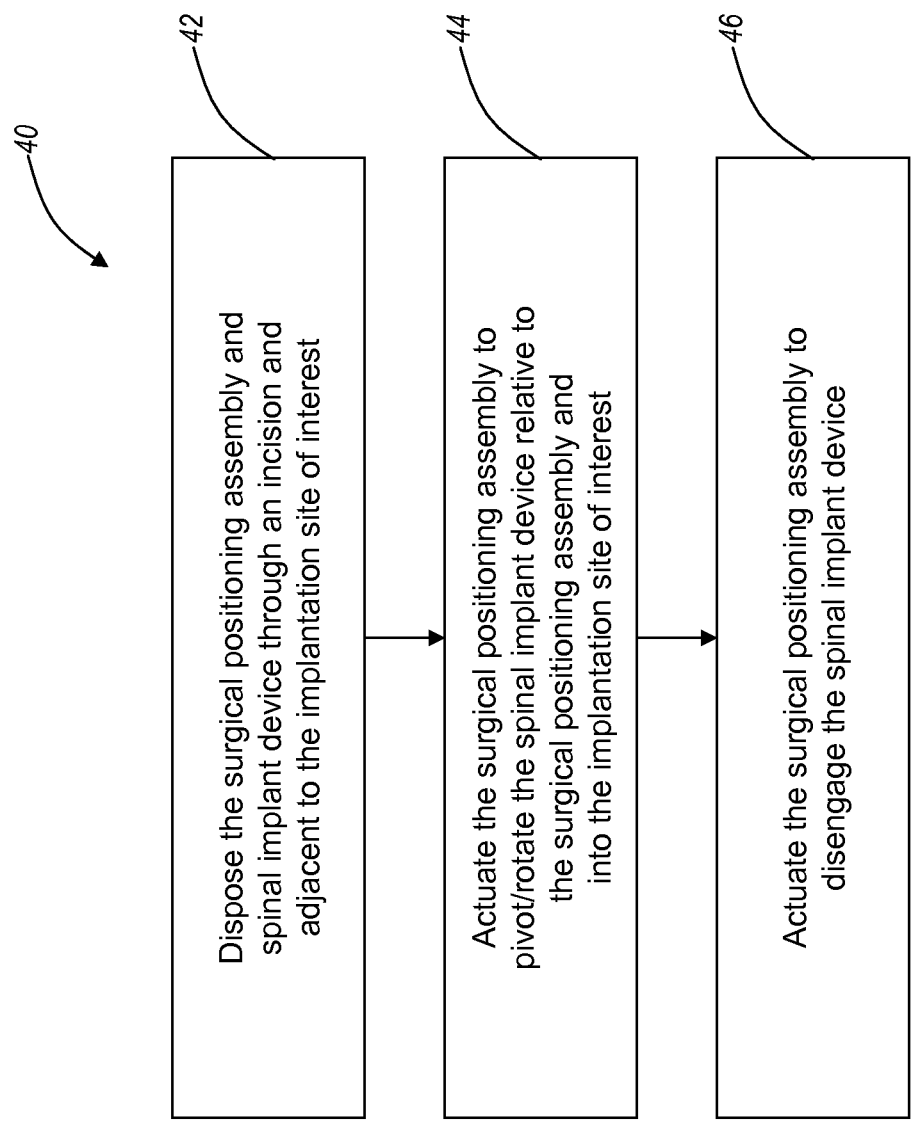
FIG. 4 is a flowchart illustrating one exemplary embodiment of the surgical positioning assembly and spinal implant device method of the present invention.

Referring to FIG. 4, in one exemplary embodiment, the surgical method 40 of the present invention includes disposing the surgical positioning assembly 10 (FIGS. 1-3) and spinal implant device 12 (FIGS. 1-3) through an incision and adjacent to the implantation site of interest along a first axis (Block 42). Next, the surgical positioning assembly 10 is actuated to pivot/rotate the spinal implant device 12 relative to the surgical positioning assembly 10 and into the implantation site of interest along a second axis that is disposed at an angle to, substantially perpendicular to, and/or simply rotated with respect to the first axis (Block 44). Finally, the surgical positioning assembly 10 is actuated to disengage the spinal implant device 12 from the surgical positioning assembly 10 (Block 46).

Although the present invention is illustrated and described herein with reference to preferred embodiments and specific examples thereof, it will be readily apparent to those of ordinary skill in the art that other embodiments and examples may perform similar functions and/or achieve like results. For example, the surgical positioning assembly of the present invention may be used to place any suitable implant device within any suitable implantation site, cage or non-cage/spinal or non-spinal, and the first and second axes along which access and placement are carried out may be those associated with any suitable surgical approach, provided that the second axis is disposed at an angle to, substantially perpendicular to, and/or simply rotated with respect to the first axis via the actuation of the surgical positioning assembly. All such equivalent embodiments and examples are within the spirit and scope of the present invention, are contemplated thereby, and are intended to be covered by the following claims.

What is claimed is:

1. A surgical positioning assembly operable for positioning a surgical implant device within an implantation site in the body of a patient through an incision and/or portal, comprising:
    a grip operable for holding the surgical positioning assembly along a first axis through an incision and/or portal;
    a retention mechanism operable for selectively coupling the surgical implant device to the grip and holding the surgical implant device substantially along the first axis; and
    a pivot/rotation mechanism operable for one or more of selectively pivoting and selectively rotating the surgical implant device relative to the grip until it is substantially along a second axis that is rotated relative to the first axis, the pivot/rotation mechanism comprising:
        a knob comprising a threaded channel;
        a rod comprising a hook structure and a threaded portion, the rod configured to be received in the threaded channel, the rod extending between the knob and the retention mechanism; and
    wherein the pivot/rotation mechanism is actuated by selectively bringing the knob into contact with the grip by rotating the knob, the contact between the knob and the grip causing the hook structure to move along the first axis with respect to the knob.

2. The surgical positioning assembly of claim 1, wherein the retention mechanism comprises a saddle structure.

3. The surgical positioning assembly of claim 2, wherein the surgical implant device comprises one or more bar structures that selectively engage the one or more rod structures via the one or more hook structures and saddle structures.

4. The surgical positioning assembly of claim 1, wherein the pivot/rotation mechanism comprises one or more rod structures comprising one or more of a hook structure and a saddle structure.

5. The surgical positioning assembly of claim 4, wherein the surgical implant device comprises one or more bar structures that selectively engage the one or more rod structures via the one or more hook structures and saddle structures.

6. The surgical positioning assembly of claim 1, wherein the surgical implant device comprises an intervertebral cage.

7. A surgical positioning assembly for positioning a surgical implant device within an implantation site in the body of a patient through an incision and/or portal, comprising:
   a knob;
   a grip comprising a threaded channel, a proximal end, and a distal end, the grip operable for holding the surgical positioning assembly along a first axis through an incision and/or portal;
   a saddle structure fixedly attached to the distal end of the grip for selectively coupling with a first bar structure of the implant device;
   a rod comprising a threaded portion and a hook structure, the rod configured to be received in a threaded channel in the grip, the rod extending between the knob and a hook structure extending beyond the distal end of the grip, the hook structure for selectively coupling with a second bar structure on of the implant device;
   wherein actuation of the knob causes the rod to recede into the grip and to rotate the surgical implant device relative to the grip until it is substantially along a second axis that is rotated relative to the first axis.

8. A surgical method for positioning a surgical implant device within an implantation site in the body of a patient through an incision and/or portal using a surgical positioning assembly, comprising:
   disposing the surgical positioning assembly and surgical implant device through the incision and/or portal and adjacent to the implantation site along a first axis;
   actuating the surgical positioning assembly to rotate the surgical implant device relative to the surgical positioning assembly until the surgical implant device is positioned substantially along a second axis that is rotated with respect to the first axis by rotating the knob in a first direction to selectively bring the knob into contact with the grip, the contact between the knob and the grip causing the hook structure to move along the first axis with respect to the knob; and
   actuating the surgical positioning assembly by rotating the knob in a second direction to disengage the surgical implant device from the surgical positioning assembly.

9. The surgical positioning assembly of claim 7, wherein the surgical implant device comprises an intervertebral cage.

* * * * *